(12) United States Patent
Gabka (10) Patent No.: US 9,532,616 B2
(45) Date of Patent: Jan. 3, 2017

(54) FOOT LOOP

(71) Applicant: Jane Gabka, New Orleans, LA (US)

(72) Inventor: Jane Gabka, New Orleans, LA (US)

(*) Notice: Subject to any disclaimer, the term of this patent is extended or adjusted under 35 U.S.C. 154(b) by 0 days.

(21) Appl. No.: 14/752,791

(22) Filed: Jun. 26, 2015

(65) Prior Publication Data

US 2015/0374047 A1 Dec. 31, 2015

Related U.S. Application Data

(60) Provisional application No. 62/017,814, filed on Jun. 26, 2014.

(51) Int. Cl.
*A41D 13/06* (2006.01)
*A44C 15/00* (2006.01)
*A61F 13/06* (2006.01)
*A41B 11/12* (2006.01)

(52) U.S. Cl.
CPC ............... *A41D 13/06* (2013.01); *A41B 11/12* (2013.01); *A44C 15/009* (2013.01); *A61F 13/065* (2013.01); *A61F 13/068* (2013.01)

(58) Field of Classification Search
CPC ..... A63B 71/1225; A41B 11/00; A41B 11/12; A41B 11/02; A61F 7/02
USPC ............... 2/455, 22, 239, 240, 241; 607/111
See application file for complete search history.

(56) References Cited

U.S. PATENT DOCUMENTS

| | | | |
|---|---|---|---|
| 1,156,621 A | 10/1915 | O'Dwyer | |
| 1,462,534 A | 7/1923 | Clarke | |
| 2,013,757 A | 9/1935 | Jung, Jr. | |
| 2,292,643 A | 8/1942 | Layana | |
| 2,708,930 A | 5/1955 | Lowman | |
| 6,454,733 B1 | 9/2002 | Krusenklaus | |
| 6,886,276 B2 | 5/2005 | Hlavac | |
| 7,972,290 B1 | 7/2011 | Chisholm | |
| D673,281 S * | 12/2012 | Rust Huthmaker | D24/192 |
| 8,475,511 B2 * | 7/2013 | Snyder | A61F 7/10 607/108 |
| 8,578,634 B1 * | 11/2013 | Nguyen et al. | A61F 5/14 36/155 |
| D739,123 S * | 9/2015 | House | D2/900 |
| 2012/0035522 A1 | 2/2012 | Brown | |
| 2013/0066249 A1 | 3/2013 | Eldridge | |

* cited by examiner

*Primary Examiner* — Tejash Patel
(74) *Attorney, Agent, or Firm* — Monty Simmons; Simmons Patents (57) ABSTRACT

The disclosed technology relates to the ornamental and utilitarian features of a device configured to protect the Metatarsal-Phalanges Joints (MPJ) zone of the user's foot when wearing shoes such as dress shoes. The device defines a loop placed around the MPJ zone wherein such loop can be neutral or natural in color to minimize its impact on the style of the shoe or flashy or have its own design that can add "strappiness" or "laciness" or contrasting color. The loop forms a protective layer between the problem areas (e.g. side and top around the MPJ zone) of the foot and the shoe material.

20 Claims, 6 Drawing Sheets

FOOT LOOP

CLAIM TO PRIORITY

This application claims priority to provisional application 62/017,814, filed on 26 Jun. 2014, of which the entire contents of such reference are incorporated herein by this reference for all that it discloses for all purposes.

TECHNICAL FIELD

The inventions relate to the ornamental and utilitarian design of fashionable protective wraps configured to protect specific areas of a user's foot.

BACKGROUND OF THE INVENTION

Proper fit is always an issue with women's shoes. Women frequently forego comfort for the sake of style. Not only are such stylish shoes uncomfortable, they can cause callous formations, bruises, and cuts around the metatarsal/phalanges joints (MPJ). There are at least three causes of such discomfort and callous formations. A first cause is improper fit. A second cause is the shoe material rubbing against the delicate skin of the foot for long periods of time. A third cause is the design cut of certain styles of shoes.

With regard to proper fitment of a shoe, one of the most common women's shoe fitment issues relate to the fit around the MPJ zone. While shoe manufacturers offer the standard widths of narrow, medium, and wide such size gradation is insufficient to account for width variations within those categories. A woman's foot that fits a medium, for example, might still feel a painful rubbing at the MPJ zone, and going to the next width category is not an option (the shoe would not stay on the foot). Further, it is very common that one foot is wider than the other (due to bunions, bunionettes or natural asymmetry) making shoe size selection more difficult as no shoe manufacturer or supplier will sell individual shoes as opposed to pairs of shoes, ie. It's not possible to buy a left foot medium and right foot wide without buying two pairs of shoes. And even if they did, the size gradations are too crude leaving the person again to buy a tighter shoe and suffer the pain or buy a wider shoe that flops around.

With regard to shoe material, some shoe materials often cause skin irritation even if the shoe is a perfect fit. The edge of the shoe material rubbing the foot can wear away the skin on the top of the foot where it comes in contact. The constant shifting of weight while walking pushes the foot into the edge of the shoe effectively turning the top of the shoe material into a planer.

With regard to shoe style, the above problems can be exacerbated by certain popular styles of women's shoes including flats, pumps, and any other high heel style shoe.

Prior art solution to the above identified problems include: 1) endure the pain—the majority of women just simply endure the pain, 2) wear less fashionable shoes—women can wear less fashionable shoes than they otherwise would desire, 3) local cover—women can use products such as band-aids® or mole-skin® that are unattractive and cover only a small portion of the trouble area do not reliably stay in place and are not resusable. Similarly, two widely known prior art solutions that are not feasible for women's dress shoes include: 1) socks—they cannot be worn with fancier shoe styles and socks cover the entire foot (not desirable), and 2) panty hose—they are often too sheer and don't provide enough protection.

What is needed is a loop of material that covers substantially all of the trouble area but only the trouble areas where such loop can be neutral or natural in color to minimize its impact on the style of the shoe or flashy or have its own design that can add "strappiness" or "laciness" or contrasting color. Such a foot loop could be designed to change the look of the shoe in many ways since many styles are envisioned. Additionally, appliqués will be available to add another dimension to the look if such is desired.

The disclosed to ornamental and utilitarian technologies address at least the above identified problems by forming a protective layer between the problem areas (e.g. side and top around the MPJ zone) of the foot and the shoe material.

SUMMARY OF THE INVENTION

Some of the objects and advantages of the invention will now be set forth in the following description, while other objects and advantages of the invention may be obvious from the description, or may be learned through practice of the invention.

Broadly speaking, a principle object of the present invention is to allow people to wear any style of shoe without pain in the area of the metatarsal/phalanges joints (MPJ) zone.

Another general object of the present invention is to provide a way of reducing/minimizing pain to the MPJ zone of a person's foot in a fashionable way.

Another general object of the invention is to provide protection for the pinky toe from corns and callouses.

Still another general object of the invention is to provide a way to enhance the style of a shoe even if it is a comfortable shoe.

For one embodiment, elastic lace ribbon is sewn into a loop and gathered. The gathers encourage the Foot Loop to conform to the shape of the foot. Appliqués may be added over the gathers for further decoration. An anti-slide element (e.g. Silicone dots) may be added where the Foot Loop meets the sole of the shoe to minimize slippage and add stability of the foot in the shoe.

Additional objects and advantages of the present invention are set forth in the detailed description herein or will be apparent to those skilled in the art upon reviewing the detailed description. Also, it should be further appreciated that modifications and variations to the specifically illustrated, referenced, and discussed steps, or features hereof may be practiced in various uses and embodiments of this invention without departing from the spirit and scope thereof, by virtue of the present reference thereto. Such variations may include, but are not limited to, substitution of equivalent steps, referenced or discussed, and the functional, operational, or positional reversal of various features, steps, parts, or the like. Still further, it is to be understood that different embodiments, as well as different presently preferred embodiments, of this invention may include various combinations or configurations of presently disclosed features or elements, or their equivalents (including combinations of features or parts or configurations thereof not expressly shown in the figures or stated in the detailed description).

Those of ordinary skill in the art will better appreciate the features and aspects of such embodiments, and others, upon review of the remainder of the specification.

BRIEF DESCRIPTION OF THE DRAWINGS

A full and enabling description of the present subject matter, including the best mode thereof, directed to one of ordinary skill in the art, is set forth in the specification, which makes reference to the appended figures, in which.

Repeat use of reference characters throughout the present specification and appended drawings is intended to represent the same or analogous features or elements of the present technology.

DETAILED DESCRIPTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention covers such modifications and variations as come within the scope of the appended claims and their equivalents. Other objects, features, and aspects of the present invention are disclosed in or may be determined from the following detailed description. Repeat use of reference characters is intended to represent same or analogous features, elements or steps. It is to be understood by one of ordinary skill in the art that the present discussion is a description of exemplary embodiments only, and is not intended as limiting the broader aspects of the present invention.

For the purposes of this document two or more items are "mechanically associated" by bringing them together or into relationship with each other in any number of ways including a direct or indirect physical "releasable connections" (snaps, screws, Velcro®, bolts, etc.—generally connections designed to be easily and frequently released and reconnected), "hard-connections" (welds, rivets, macular bonds, thread, generally connections that one does not anticipate disconnecting very often if at all and that generally needs to be "broken" to separate), and/or "moveable connections" (rotating, pivoting, oscillating, etc.).

This document includes headers that are used for place markers only. Such headers are not meant to affect the construction of this document, do not in any way relate to the meaning of this document nor should such headers be used for such purposes.

While the particulars of the present invention and associated technology may be more frequently described for use with women's shoes, the disclosed technology may be used with men's shoes and in any fields having the problems addressed by the various embodiments of the invention.

Figure 1:
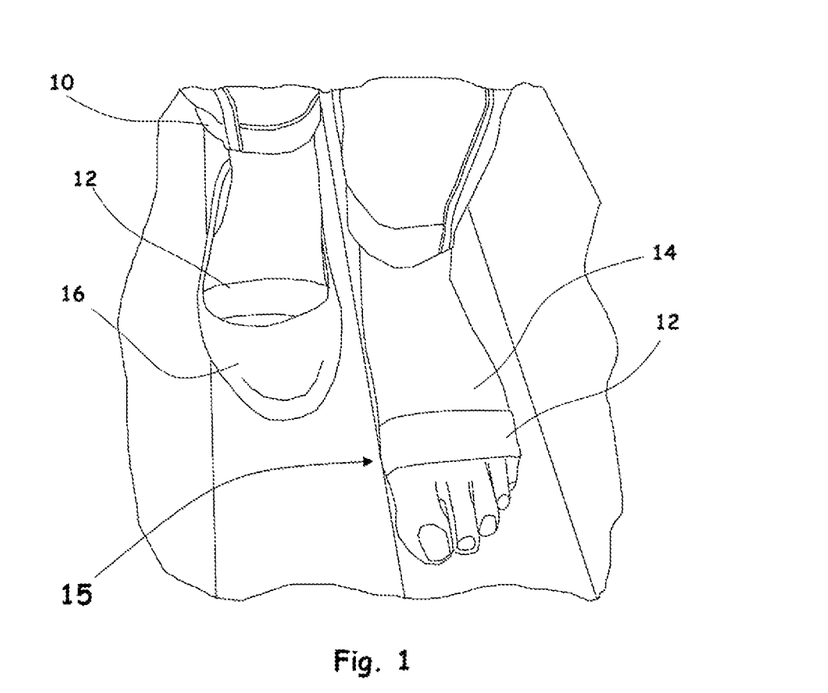
FIG. 1 is an elevated perspective view of a foot loop device being worn by a user wearing a closed toe shoe.
Figure 2:
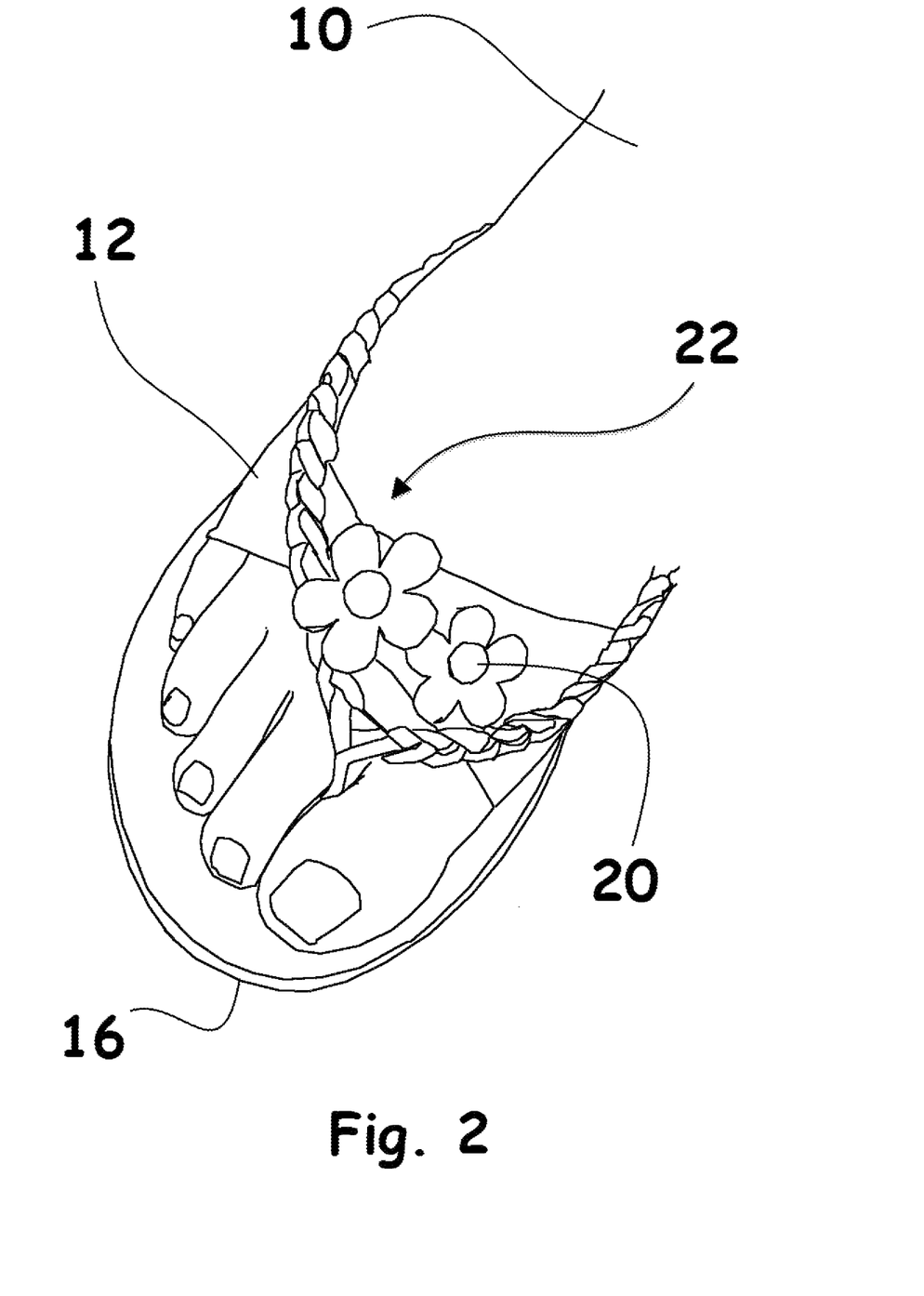
FIG. 2 is an elevated perspective view of a foot loop device being worn by a user wearing a sandal where the foot loop is gathered defining a gather interface and associated with an appliqués at such gather interface and a surface of the foot loop device.
Figure 3:
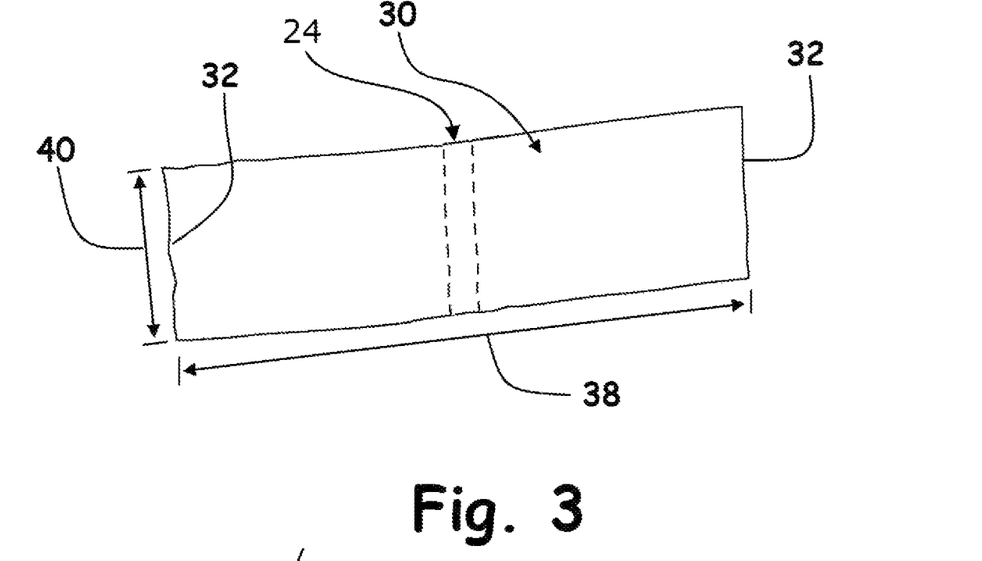
FIG. 3 is a top plan view of one side of a foot loop device defining two ends and lying long ways.
Figure 4:
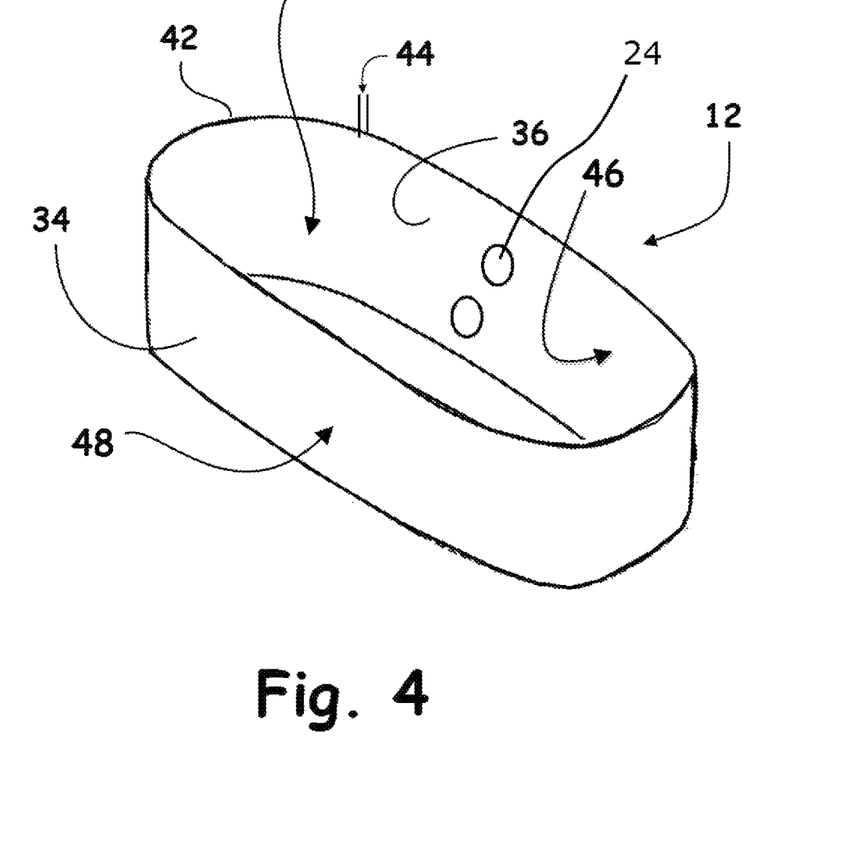
FIG. 4 is an elevated perspective view of a continuous foot loop configuration.
Figure 5:
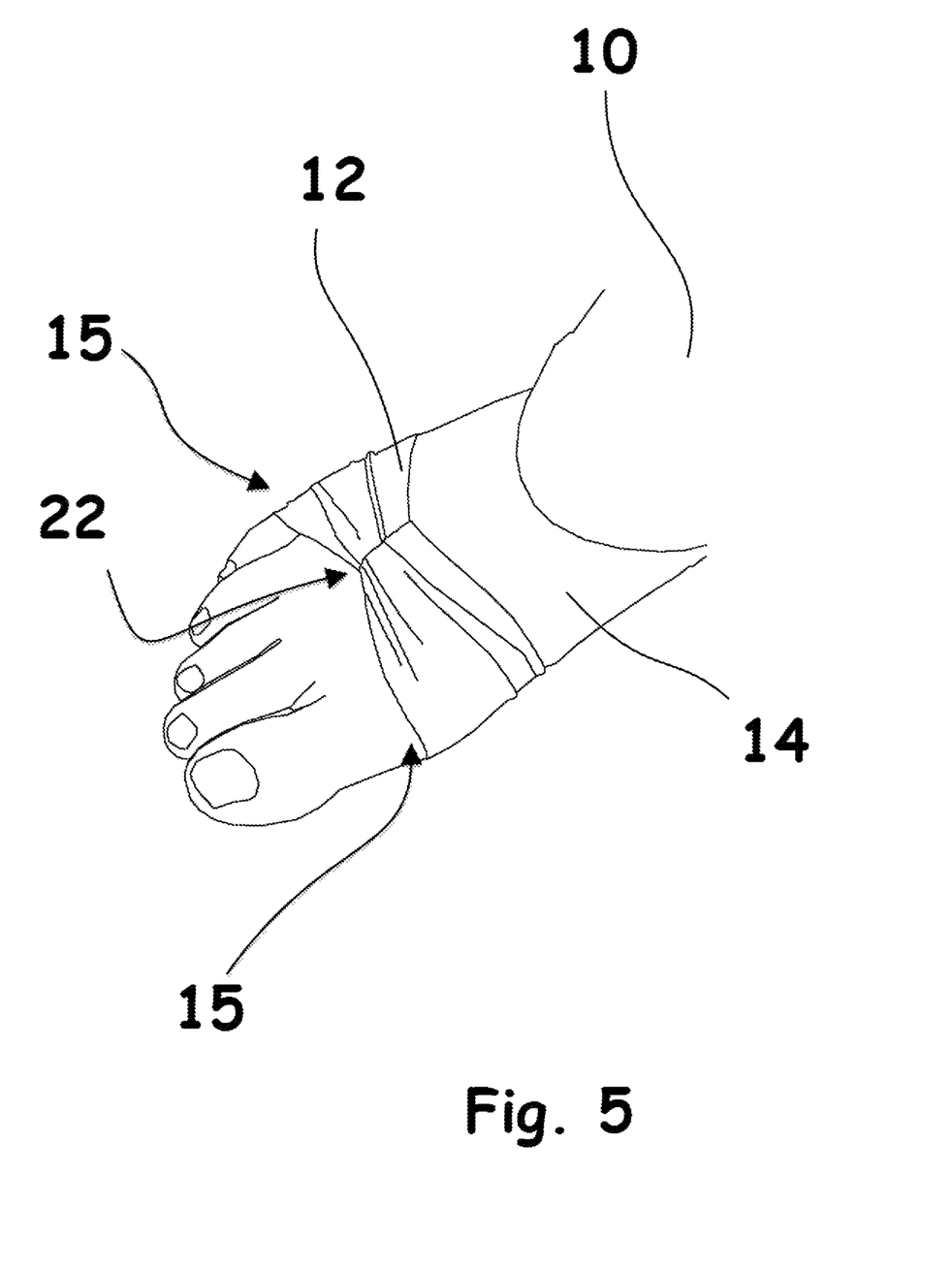
FIG. 5 is an elevated perspective view of a foot loop device defining a gather interface and being worn by a user without shoes.
Figure 6:
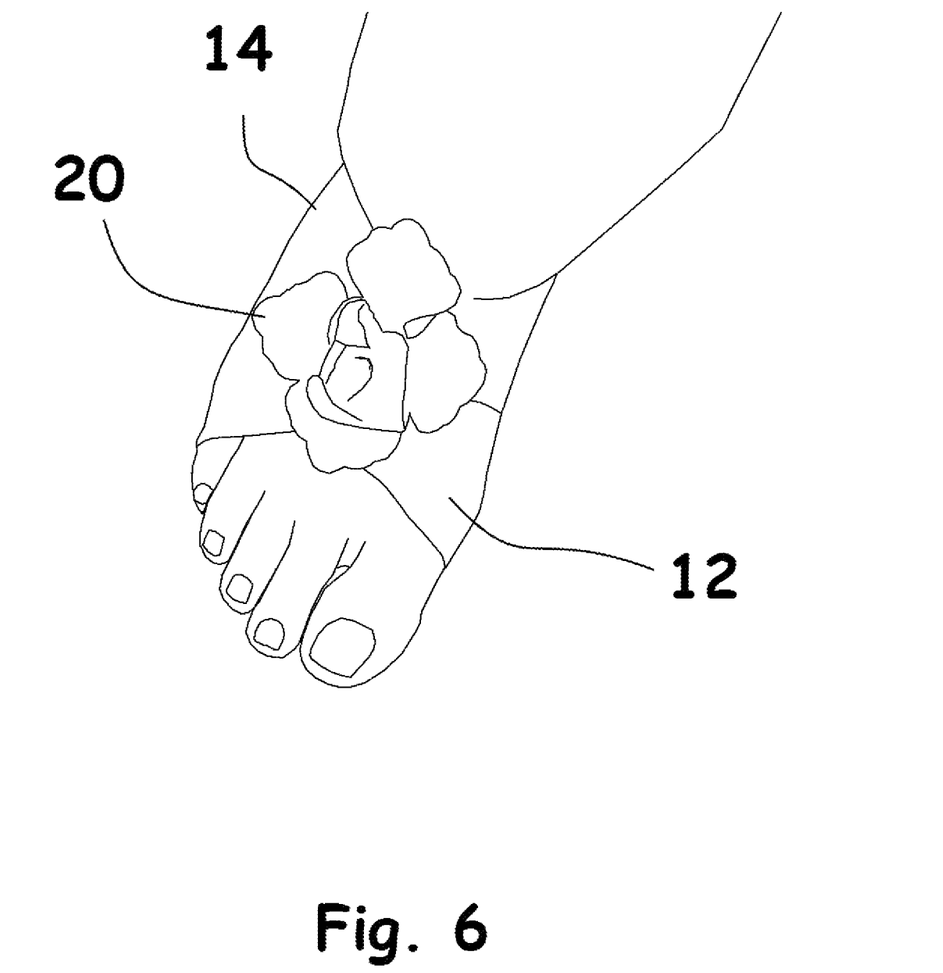
FIG. 6 is an elevated perspective view of a foot loop device being worn by a user without a shoe where such foot loop device defines a gather interface associated with a appliqué depicting a bow.
Figure 7:
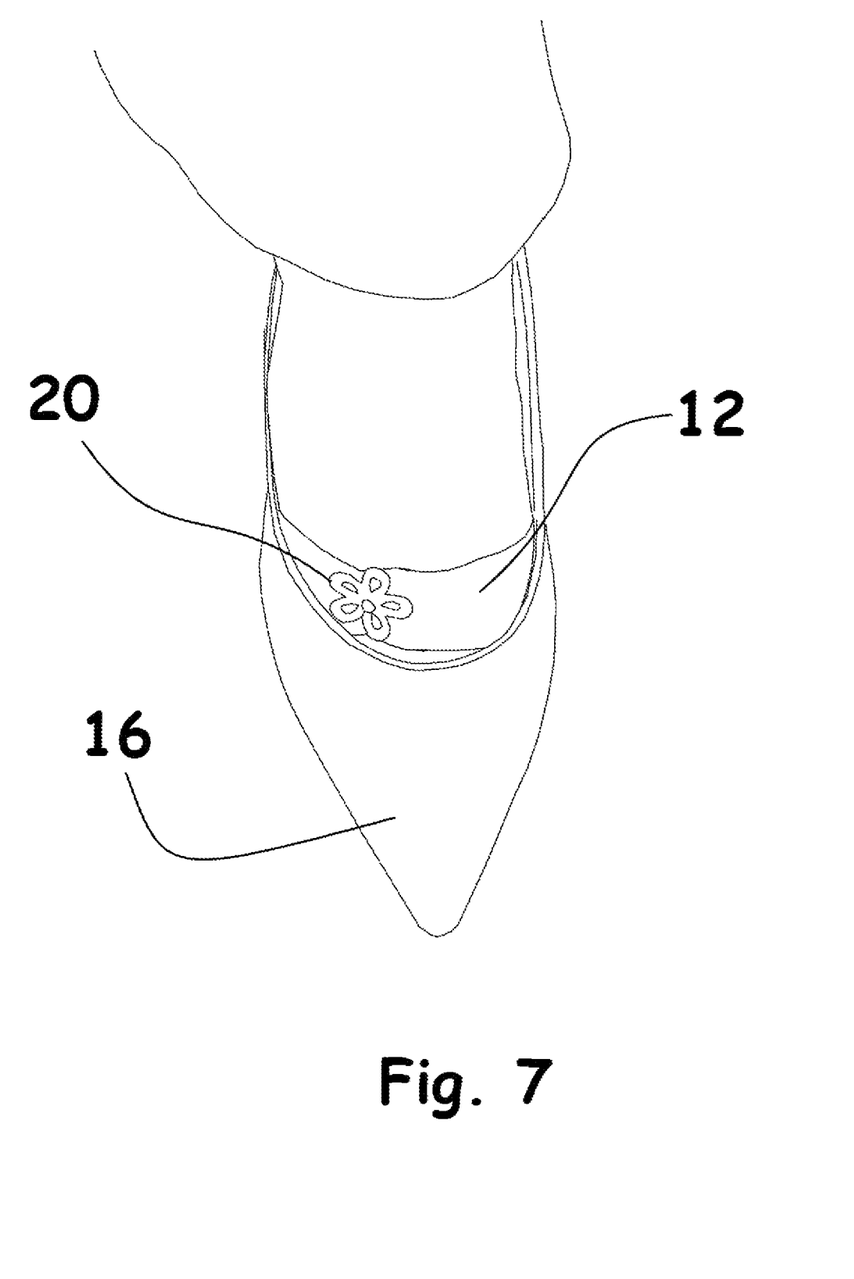
FIG. 7 is an elevated perspective view of a foot loop device being worn by a user with a closed toe dress shoe wherein an outside surface of the foot loop device is associated with an appliqué depicting a flower.

Referring now to FIG. 1 through FIG. 7, exemplary embodiments of a foot-loop (12) associated with the metatarsal-phalanges joint (MPJ) zone (15) of a user's feet (14) are presented. FIG. 1 and FIG. 7 depict foot-loop (12) being worn with enclosed end shoes whereas Fig. depicts foot-loop (12) being worn with open end shoes such as sandals. FIG. 5 and FIG. 6 depict a person wearing a foot-loop (12) without shoes. FIG. 2 and FIG. 5 further depict foot-loop (12) defining a fetching-interface (22) which may be configured for being associated with a bling-accessory (20) as described in more detail below.

Viewed differently, as depicted in FIG. 3 and FIG. 4, the foot loop (12) is configured for protecting Metatarsal-Phalanges Joints (MPJ) zone (15) of the user's foot and comprises an elongated body (30) comprising a first body surface (34) and an opposing second body surface (36) configured in the shape of a loop thereby defining a center void (26) and an inner body surface (46) and an outer body surface (48) thereby defining a body perimeter length (the distance around the loop) and a body width (40) and wherein said first surface and said second surface are connected by a peripheral edge (42) thereby defining a body thickness (44).

As best seen in FIG. 3 and FIG. 4, for the currently preferred embodiment, foot-loop (12) defines an elongated body (30) comprising a first body surface (34) and an opposing second body surface (36) defining two opposing body ends (32), a body length (38) and a body width (40). The first body surface (34) and the second body surface (36) are connected by a peripheral edge (42) thereby defining a body thickness (44). Preferably elastic stitching extends throughout substantially all of the elongated body.

Still referring to FIG. 3 and FIG. 4, for one embodiment at least one of the first body surface (34) and the second body surface (36) define a movement-inhibiter (24) preferably disposed 180 degrees from the fetching interface (22) (for embodiments have a fetching interface). One of ordinary skill in the art will appreciate that the movement-inhibiter (24) is ideally disposed along elongated body (30) where the body-loop is to meet the sole of the shoe (out of sight when in use). As depicted in FIG. 3 the movement-inhibiter (24) may define a band or zone which may run parallel to ends (32) as depicted in the FIG. 3 and/or perpendicular to ends (32) (ideally not the full length of the elongated body (30)—just long enough to cover the section of the surface intended to be between the bottom of the foot and the sole of the shoe—out of sight). Alternatively, as depicted in FIG. 4 the movement-inhibiter may define a plurality of "spots". The spot configuration would likely be more accommodating to stretching of the elongated body (30) for some movement-inhibiter materials. Suitable materials include Toughtek non-slip fabric, grip cloth, and silicone. Embodiments where the entire body loop is composed of non-slip material fall within the scope and spirt of the invention.

The two opposing ends (32) are mechanically associated together to define a foot-loop structure thereby defining an inner body surface (46) and an opposing outer body surface (48). The two opposing body ends (32) may be sewn together using a sewing-element such as a string or thread or releasably mechanically associated together using an attachment element. It will be appreciated that either first body surface (34) or second body surface (36) may define either of inner body surface (46) and out of body surface (48).

As depicted in FIG. 3, the two opposing body ends (32) are sewn together to define a fetching-interface (22, FIG. 5). Alternatively, the two body ends (32) may be releasably mechanically associated using an attachment element which may also define a fetching-interface (22). Exemplary embodiments of suitable attachment elements include tape, hook, glue, and Velcro. As depicted in FIG. 2 and FIG. 6, for one embodiment the fetching interface (22) may be configured for receiving body-bling. Alternatively, the body-loop may define the body-bling. Examples of body-bling include jewelry and patterns/applique (e.g. flowers, bows, etc.) or representational scenes sewn into the body-loop and perhaps created by the attachment smaller pieces of fabric to larger pieces of contrasting color or textures. For example, in FIG. 2 and FIG. 7 the fetching-interface (22) is associated with body-bling (20) in the shape of flowers. Such body bling may be activity specific such as boxing gloves used when one is attending a fighting activity or a football used when one is attending a football game. It should be appreciated that the outer body surface (48) may also be configured for being associated with body-bling (20).

Notably, as depicted in FIG. 4, for one alternative embodiment, the "ends" (32) may be woven into the foot-loop (12) thereby defining a continuous loop suitably sized and composed of a suitable material so that the foot-loop securely wraps around the MPJ zone (15) of a user's feet (14).

As best seen in FIG. 3 though FIG. 5, the foot-loop (12) defines a body length (38) and a body width (40) suitably sized so that the body-loop covers substantially all of the MPJ zone (15) of the user's foot (14) when associated with the MPJ zone. Exemplary measures of the various foot-loop (12) parameters include a body-width (40) of between three-fourths of an inch to 2 inches wide and a body length (38) of between about 5 to about 13 inches in length from end to end (un-stretched) as depicted in FIG. 3. For continuous foot-loop configurations, "end-to-end" means the distance between the two ends of a cut foot-loop (12) laid out long ways as depicted in FIG. 3.

The foot loop may be sold in standard small, medium and large sizes where the small size is configured to stretch comfortably to the medium size, and the medium size is configured to stretch comfortably to the large size. For example, the small size may be 5 inches long un-stretched and configured to stretch to 9 inches long. The medium would be 9 inches long and configured to stretch to 13 inches long. Any size divisions may be used without departing from the scope and spirit of the invention.

Embodiments of foot-loop (12) include a lace loop made of lace material approximately 0.10 mm thick, and a jersy loop made of jersy material approximately 0.12 mm thick, and a velvet loop made of a velvet material approximately 0.27 mm thick. The thickness of the foot loop may be any thickness desired by the user but a typical thickness is expected to be between about 10 micrometers to 0.8 mm thick.

Lace is a delicate fabric made of yarn or thread in an open web-like pattern. Lace is typically made from cotton thread but may be made using linen, silk, gold, or silver threads as well as synthetic fiber. For the purposes of this document, cotton, linen, silk, or synthetic fibers are preferred. With regard to "jersy" fabric, such fabric is a knit fabric made of at least one of wool, cotton, and synthetic fibers. Similarly, "velvet" is a type of woven tufted fabric in which the cut threads are evenly distributed, with a short dense pile, giving it a distinctive feel. Velvet can be made from either synthetic or natural fibers.

For one exemplary embodiment, foot loop (12) elongated body (30) first surface (34) and second body surface (36) are composed of the same material and define the same design. For such embodiment the first surface and second surface my define either of the inner body surface or the outer body surface and they may be reversed to change positions. The body-loop is preferably made from slightly flexible thin material that could be fabric, polyurethane, or other suitable material and can have multiple designs, color, and patterns to mimic skin tones, shoe straps, or other design and aesthetic objectives.

Alternatively, the first body surface (34) may define a wicking surface and the second body surface (36) may define a comfort surface. A wicking surface transfers moisture from the user's foot to the outer body surface (48). A comfort surface is configured to enhance a user's comfort while wearing shoes (such as adding padding). For one embodiment, such functionality is achieved in a layering system. The inner body surface (46) (base layer) defines a wicking layer that moves moisture (perspiration) away from the user's foot to the outer body surface (48) and the outer body surface (48) would define the comfort surface such as a padded protective and optionally waterproof layer.

Such wicking configuration should be moisture wicking to keep the interface between the body-loop and the foot skin dry so as to reduce slippage while the other surface is designed to wick moisture away from the user's foot. The material is ideally made through an industrial process to produce a kind of tape or strap, i.e. a narrow slightly stretchy and soft material with one side is designed to wick away moisture which helps keep it in place and comfortable.

Finally, one of ordinary skill in the art will appreciated that ideally Foot Loop is sewn into a loop and would is made of stretchy fabric so it can slip on and off while still holding on tight. For embodiments where the foot loop is "hooked" together and not forming a permanent loop the fabric can have less give or no give compared to the more "permanent" loop configurations. Further, the foot loop may be worn with shoes where the foot loop is completely out of sight during use. For such a configuration, fetching interfaces and loop-bling are less important and may not be included in the design.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A strap configured for wrapping around a user's foot, said strap comprising:
an elongated body defining two opposing body ends wherein said elongated body comprises a first body surface and an opposing second body surface defining a body length and a body width wherein said first surface and said second surface are connected by a peripheral edge thereby defining a body thickness and wherein elastic stitching extends throughout said body;
wherein said two opposing body ends are mechanically associated together to define a body-loop thereby defining an inner body surface and an outer body surface and wherein the two opposing body ends are one of (a) sewn together using a sewing-element and (b) releasably mechanically associated together using an attachment element; and wherein said body length and said body width are suitably sized so that said body-loop covers the Metatarsal/Phalanges Joints (MPJ) zone of the user's foot when associated with the MPJ zone of said user's foot; and wherein said body-loop defines one of (a) a lace loop about 0.10 mm thick, (b) a jersey loop about 0.12 mm thick, and (c) a velvet loop about 0.27 mm thick.

2. A strap configured for wrapping around a user's foot as in claim 1, wherein said two body ends are sew together with a thread thereby defining a fetching interface.

3. A strap configured for wrapping around a user's foot as in claim 2, wherein at least one of (a) said elongated body further defines body-bling at said fetching interface, (b) said outer body surface is configured for being associated with body-bling, and (c) said fetching interface is configured for being associated with body-bling.

4. A strap configured for wrapping around a user's foot as in claim 3, wherein said body-bling in jewelry.

5. A strap configured for wrapping around a user's foot as in claim 3, wherein said body-bling defines one of (a) an appliqué, (b) a bow, and (c) stitching in the shape of bling icon.

6. A strap configured for wrapping around a user's foot as in claim 1, wherein said elongated body defines a layered configuration wherein said first body surface defines a wicking surface and said second body surface defines a comfort surface.

7. A strap configured for wrapping around a user's foot as in claim 1, wherein the outer surface defines a movement-inhibiter.

8. A strap configured for wrapping around a user's foot as in claim 1, wherein said outer surface defines an movement-inhibiter.

9. A strap configured for wrapping around a user's foot as in claim 8, wherein said movement-inhibiter comprises silicone dots.

10. A foot loop configured for protecting the Metatarsal-Phalanges Joints (MPJ) zone of the user's foot, said foot-loop comprising:

an elongated body comprising a first body surface and an opposing second body surface configured in the shape of a loop thereby defining a center void and an inner body surface and an outer body surface thereby defining a body perimeter length and a body width and wherein said first surface and said second surface are connected by a peripheral edge thereby defining a body thickness;

wherein said body perimeter length and said body width are suitably sized so that said elongated body covers substantially all of the MPJ zone of the user's foot when associated with the MPJ zone of said user's foot and wherein said loop defines one of (a) a loop about 0.10 mm thick, (b) a loop about 0.12 mm think, or (c) a loop about 0.27 mm thick.

11. A foot loop as claimed in claim 10, wherein elastic stitching extends throughout substantially all of said elongated body.

12. A foot loop as claimed in claim 11, wherein at least one of said first body surface and said second body surface defines a fetching interface.

13. A foot loop as claimed in claim 12, wherein the inner body surface and outer body surface are reversible.

14. A foot loop as claimed in claim 12, wherein said fetching interface is one of (a) configured for being associated with body-bling, and (b) defines body-bling.

15. A foot loop as claimed in claim 12, wherein said elongated body defines a layered configuration wherein said first body surface defines a wicking surface and said second body surface defines a comfort surface.

16. A foot loop as claimed in claim 10 wherein said outer surface defines a movement-inhibiter.

17. A foot loop as claimed in claim 16 wherein said movement-inhibiter comprises silicone dots.

18. A method of protecting the Metatarsal-Phalanges Joints (MPJ) zone of the user's foot when wearing shoes, said method comprising the steps of:

configuring an elongated body in the shape of a loop defining a center void, said elongated body comprising an inner body surface and an outer body surface thereby defining a body perimeter length and a body width and wherein said inner body surface and said outer body surface are connected by a peripheral edge thereby defining a body thickness wherein said loop defines at least one member from the group comprising: (a) a loop about 0.10 mm thick, (b) a loop about 0.12 mm thick, and (c) a loop about 0.27 mm thick; and selecting a body perimeter length and a body width suitably sized so that said elongated body covers the MPJ zone of the user's foot when associated with the MPJ zone of said user's foot.

19. A method of protecting the Metatarsal-Phalanges Joints (MPJ) zone of the user's foot as claimed in claim 18, wherein elastic stitching extends throughout said elongated body.

20. A method of protecting the Metatarsal-Phalanges Joints (MPJ) zone of the user's foot as claimed in claim 19, wherein said elongated body defines a fetching interface and a movement-inhibiter disposed about 180 degrees apart along said loop and wherein the inner body surface and outer body surface are reversible.

* * * * *